(12) United States Patent
Vernizeau et al.

(10) Patent No.: US 9,101,719 B2
(45) Date of Patent: Aug. 11, 2015

(54) PISTON ROD FOR A CONTAINER

(75) Inventors: Michel Vernizeau, Valence (FR); James Pellegrini, Cary, NC (US); Frédéric Perot, Saint Paul de Varces (FR)

(73) Assignee: Becton Dickinson France, Le Pont-de-Claix (FR)

( * ) Notice: Subject to any disclaimer, the term of this patent is extended or adjusted under 35 U.S.C. 154(b) by 75 days.

(21) Appl. No.: 13/824,720

(22) PCT Filed: Oct. 29, 2010

(86) PCT No.: PCT/IB2010/003169
§ 371 (c)(1),
(2), (4) Date: May 28, 2013

(87) PCT Pub. No.: WO2012/056265
PCT Pub. Date: May 3, 2012

(65) Prior Publication Data
US 2013/0253435 A1    Sep. 26, 2013

(51) Int. Cl.
*A61M 5/315*    (2006.01)
*A61M 5/00*    (2006.01)
*A61M 5/50*    (2006.01)
*A61M 5/31*    (2006.01)

(52) U.S. Cl.
CPC ........... *A61M 5/31511* (2013.01); *A61M 5/002* (2013.01); *A61M 5/5086* (2013.01); *A61M 2005/3104* (2013.01); *A61M 2005/31518* (2013.01)

(58) Field of Classification Search
CPC ............ A61M 5/315; A61M 5/31511; A61M 5/31515; A61M 2005/31518; A61M 5/002; A61M 5/5086; A61M 2005/3104
USPC .................................. 604/192, 187, 218–235
See application file for complete search history.

(56) References Cited

U.S. PATENT DOCUMENTS

| 4,011,868 A | 3/1977 | Friend |
| 6,059,756 A * | 5/2000 | Yeh ................................ 604/218 |
| 2011/0222366 A1 | 9/2011 | Axen et al. |

FOREIGN PATENT DOCUMENTS

| DE | 188449 | 10/1906 |
| WO | 2010034462 A1 | 4/2010 |

* cited by examiner

*Primary Examiner* — Aarti B Berdichevsky
*Assistant Examiner* — Laura Schell
(74) *Attorney, Agent, or Firm* — The Webb Law Firm

(57) ABSTRACT

A piston rod for an injection device, including first and second legs, each leg being foldable on itself and including a proximal region. The piston rod is capable of transitioning from a folded position to an unfolded position, and includes a mechanism for coupling the proximal regions of the legs when the piston rod is in the unfolded position. The invention also relates to a kit which includes the piston rod.

26 Claims, 6 Drawing Sheets

PISTON ROD FOR A CONTAINER

Figure 1:
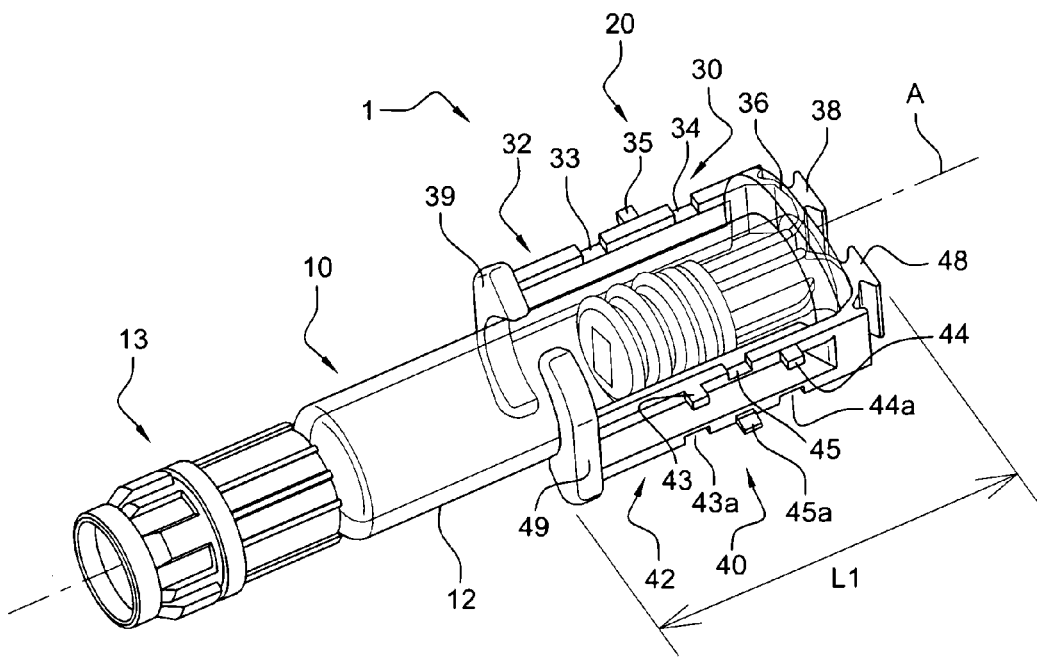

The present invention relates to a piston rod to be used with a container in view of forming an injection device that can be stored in a compact configuration.

In this application, the distal end of a component or of a device means the end furthest away from the hand of the user and the proximal end means the end closest to the hand of the user, when the component or device is in the use position. Similarly, in this application, the terms "in the distal direction" and "distally" mean in the direction of the injection, and the terms "in the proximal direction" and "proximally" mean in the direction opposite to the direction of injection.

Injection devices, such as syringes, are well known. Many different types of injection devices have been designed for administering medicines. Injection devices usually comprise a container intended to receive the product to be injected and a piston rod intended to move a piston within the container so as to expel the product therefrom at the time of injection. Empty and pre-filled disposable injection devices exist but prefilled devices are now preferred because they are convenient, safe and efficient and may be used directly in emergency cases.

Prefilled injections devices are filled by a pharmaceutical company, packaged for use, and then typically stored at a doctor's office, hospital, etc. until they are needed for use. In such a condition, the prefilled injection device will take up a predetermined amount of storage space based upon the size of the injection device (typically comprised of a syringe barrel, a piston, a piston rod, and possibly a needle). In some cases, the predetermined amount of storage space the injection device will take up is a maximum space approximating the length of the piston rod, plus the length of the syringe barrel, plus the length of the needle (if provided).

Required storage space is an important feature for prefilled injection devices. It is especially important when the medicine contained in these devices must be stored and transported at low temperatures. Storage of these injection devices may require refrigeration and can be expensive. This is especially the case in hospitals and pharmacies, where storage space for medicines is limited.

Thus, there is a need for an injection device which would be particularly compact, particularly when the injection device is prefilled. There is a need for an injection device that can be packaged in a very compact way.

Solutions of the prior art have consisted in providing the piston rod separated from the container, or in providing the piston rod with a hinge so as to fold it along the container, thereby reducing the overall length of the device to be packaged. U.S. Pat. No. 4,011,868 describes such an injection device.

Nevertheless, the injection devices of the prior art still occupy a large volume, at least in width, but also in length, depending on the shape of the piston rod, and they present a less desirable solution, because their outer shape is not symmetrical.

There is therefore also the need for a compact injection device having an outer shape occupying the smallest volume possible and being easy to store with other devices having the same volume/shape, so that as little space as possible is wasted when a large number of these devices is stored, for example in an inventory of a hospital or a pharmacy.

Moreover, such an injection device must be simple to use, and preferably would not alter the typical process followed by a caregiver when administering an injection.

An aspect of the present invention is therefore to provide a piston rod, to be used to form an injection device, for example in combination with a container, of simple use for the user, that reduces the overall length and volume of the injection device in the storage position of the injection device, even in the case where the container of the injection device is prefilled with a medicine. Another aspect of the invention is to provide a piston rod capable of being easily manufactured industrially and easily assembled on a container. Another aspect of the invention is to provide a piston rod that is reliable and allows a continuous and complete injection.

An aspect of the invention is a piston rod for an injection device, said piston rod comprising a first and a second legs, each leg comprising a bendable part and extending substantially proximally from a junction element at which a distal end of each of the first and second legs meet, each leg being capable of being folded at the location of its bendable part, said piston rod having a globally elongated shape substantially aligned on a longitudinal axis A and being in one of a folded position, in which said piston rod has a first length, and an unfolded position, in which said piston rod has a second length that is different from said first length, wherein when said piston rod is in said folded position, the first and second legs are folded at their respective bendable part, and an area of each leg, proximally spaced from said bendable part, substantially faces the junction element, wherein when said piston rod is in said unfolded position, said areas of said first and second legs face each other, said piston rod further comprising coupling means for coupling said areas with each other when said piston rod is in said unfolded position.

In this application, the distal end of the piston rod or of a leg of said piston rod means the end furthest away from the hand of the user and the proximal end means the end closest to the hand of the user, when the piston rod is in the use position, in other words in the unfolded position. Similarly, in this application, the terms "axially spaced" refer to the longitudinal axis A of the piston rod when said piston rod is in its use position, i.e. its unfolded position.

Another aspect of the invention is a kit comprising such a piston rod and a container intended to receive a product to be injected, said container comprising a tubular barrel provided at its distal end with a port intended to receive an injection needle, said product being intended to be expelled from said tubular barrel under distal displacement of a piston movable within said tubular barrel by said piston rod.

As will appear from the description that follows, the piston rod of the invention is capable of being folded over the tubular barrel of a container it is used in combination with. Indeed, the piston rod of the invention is capable of being switched from a folded position, in which it has a first length and preferably a relatively compact shape, to an unfolded position, which is also its use position, in which it has a second length and preferably a globally elongated shape. As such, the first length is preferably less than the second length. Moreover, as will appear from the description below, because the shaft of the piston rod of the invention is reconstituted in its in use position from a plurality of, i.e. at least two, legs, the volume occupied by these legs in the folded position of the piston rod is equally distributed around the container and gives a relatively regular and symmetrical outer shape, such as a globally cylindrical shape, of the injection device in its storage position, thereby enabling an easy packaging and a compact storage of a large number of pre-packaged injection devices.

In embodiments, the coupling means includes at least a first and a second fixing means, said first and second fixing means being axially spaced apart from each other in said unfolded position of the piston rod.

Such embodiments provide for a very reliable reconstituted shaft for the piston rod in its unfolded position. Indeed, the fact that the piston rod comprises two fixing means axially spaced apart from each other ensures that there is no sliding of the proximal region of one leg with respect to the proximal region of the other leg in the use position of the piston rod. In consequence, the reconstituted shaft of the piston rod is rigid and reliable: there is no risk that the piston rod divert from the axial direction of the injection device when the user pushes distally on the piston rod at the time of use. Such an embodiment rigidifies the reconstituted piston rod.

The coupling means may further include a third fixing means, said first, second and third fixing means being axially spaced apart from one another in said unfolded position of the piston rod. Such an embodiment allows obtaining a very reliable piston rod in its use or unfolded position. In other embodiments, the coupling means may include more than three fixing means, all axially spaced apart from one another.

In embodiments, the coupling means is located on said area of only one of said first and second legs. For example, the coupling means may be adhesive means, such as a plurality of points of glue axially spaced apart from one another and located on said area of the first leg, intended to stick to said area of the second leg in the unfolded position of the piston rod. The points of glue may be covered in the folded position of the piston rod by a protection film to be removed at the time the user reconstitutes the piston rod for use.

In alternative embodiments, the coupling means are located partly on said area of said first leg and partly on said area of said second leg. For example, each of said first, second and optionally third fixing means is a snap-fit means, each snap-fit means including a peg and a corresponding recess intended to be engaged into one another in said unfolded position of said piston rod, said peg being located on said area of one of said first and second legs, said recess being located on said area of the other of said first and second legs.

In embodiments, said coupling means comprises snap-fit means comprising a peg and a recess engageable with each other when said piston rod is in said unfolded position, said peg being located on said area of one of said first and second legs, said recess being located on said area of the other one of said first and second legs In embodiments, the coupling means may comprise a combination of snap-fit means and of adhesive means.

In embodiments, at least one of said first and second legs is provided at its proximal end with a transversal wall. Such an embodiment allows forming a pushing surface for the user for exerting a distal pressure on the piston rod when the piston rod is in its unfolded position and ready for use. In embodiments, each of said first and second legs is provided at its proximal end with a transversal wall. Such an embodiment allows distributing the space occupied by the pushing surface on two transversal walls, thereby rendering the overall shape of the piston rod and injection device more symmetrical and therefore easier to package, even in large numbers.

In embodiments, each of said transversal wall has a semi-circular concave shape, said semi-circular concave shape being directed towards the longitudinal axis A in the folded position of the piston rod: as will appear clearly from the following description, the concave shape allows the transversal wall to match perfectly the outer convex shape of the container the piston rod is intended to be used with: indeed, containers of injection devices, such as syringe, have usually the shape of tubular barrels.

In embodiments, each of said bendable parts comprises two hinges axially spaced apart from each other in the unfolded position of the piston rod. The bendable part of a leg of the piston rod of the invention is intended to allow the leg to be folded on itself, in particular in the manner of a U turn. Having two hinges axially spaced apart from each other allows the leg to easily do a U turn at the location of the proximal end of the container the piston rod is intended to be used with. For instance, in embodiments where the container is a tubular barrel having a flange at its proximal end, the two axially spaced apart hinges allow the leg to design around the flange so that, once the leg is folded on itself, in the folded position of the piston rod, then the proximal region of each leg can easily stand parallel close to the outer wall of the tubular barrel, thereby reducing the space needed for it to be stored and limiting the volume occupied by both the barrel and the folded legs.

In embodiments, said two hinges are linked to each other by a bridge. For example, the bridge is rigid. By "rigid" is meant herein that the bridge itself is not bendable, as opposed to the two hinges. In such embodiments, the flexibility of the bendable part is created by the fact of having two hinges axially spaced apart from each other. In a preferred embodiment, said bridge, in particular said rigid bridge, of the first leg faces the said bridge, in particular said rigid bridge, of the second leg when the piston rod is in its unfolded position. Such an embodiment, for example when the bridge is rigid, allows rigidifying the reconstituted shaft of the piston rod at the location of the bendable parts of the legs. Such an embodiment allows obtaining a rigid and reliable piston rod in the in use, i.e. unfolded, position of the piston rod.

In alternative embodiments, each of said bendable parts is made of an elastic metallic blade. As explained above, the elastic metallic blade is designed so as to be capable of forming a U turn, thereby enabling a leg to be folded over itself at the location of the metallic blade. In such embodiments, as will appear from the description below, part of the steps for reconstituting the piston rod may be performed automatically, with minimum action from the user.

In embodiments, said junction element comprises at its distal end piston attaching means. The piston attaching means may be selected from a screw, snap-fit means, glue and their combinations.

In embodiments, the piston rod further comprises one or more additional leg(s), each of said additional leg comprising a bendable part and extending proximally from said junction element where its distal end is fixed, said coupling means being designed so as to couple a proximal region of said additional leg(s) to said area of at least one of said first and second leg in the unfolded position of said piston rod. For example, the piston rod of the invention may comprise three or four legs.

In embodiments of the kit of the invention, the tubular barrel is prefilled with the product to be injected, said tubular barrel being closed at its distal end with a cap and at its proximal end by a piston. In such a case, the piston rod may be mounted on said container, the junction element of the piston rod being lodged within said tubular barrel proximally from said piston with the distal end of said junction element facing the proximal end of said piston, said piston rod being in its folded position: for example, in such a position, the bendable part of each of said first, second and optionally additional legs faces the proximal end of the tubular barrel and the proximal region of each of said first, second and optionally additional leg extend substantially parallel to the outer wall of the tubular barrel. The piston may or may not be coupled to the junction element of the piston rod.

In embodiments, said junction element of said piston rod is coupled with said piston, and the proximal region of at least one of said first and second legs extends substantially parallel to an outer wall of said tubular barrel.

In embodiments where the tubular barrel is prefilled, a needle may be present at the distal end of the tubular barrel, the needle being both closed and protected by said cap.

In embodiments, the distal end of the junction element of said piston rod is coupled to said piston.

In embodiments, the shape of each transversal wall as described above is complementary in shape to the outer shape of said tubular barrel, the complementary shape of each transversal wall and the outer shape of said tubular barrel enabling a nesting relationship between each transverse wall and said tubular barrel when said piston rod is in its folded position. For example, the concave shape of the transversal wall may be snap-fit on the tubular barrel. Such embodiments with a nesting relationship between each transverse wall and said tubular barrel allow a gain of space and reduce the overall volume occupied by the injection device in its storage position.

In embodiments, said two transversal walls are linked to each other by a breakable link in the folded position of the piston rod. In embodiments, the proximal end of each of said first and second legs extends beyond the distal end of said barrel. In such embodiments, the breakable link constitutes a tamper-evidence means of the piston rod. Indeed, the breakable link needs be broken in order to unfold the piston rod and put it in a use position: as such, if a user is provided with a piston rod in a folded position but with a broken link, he knows that the piston rod may have already been used.

These embodiments allow obtaining a very compact tamper evidence injection device. In particular, in embodiments where the proximal end of each of said first and second legs extends beyond the distal end of said barrel, the transversal walls are located beyond the distal end of the container, and no additional radial volume with respect to the volume already occupied by the barrel is used by the tamper evidence system. The outer shape of the injection device is symmetrical and allows an easy storage of a large number of product units.

In embodiments, the kit further comprises a packaging for receiving said piston rod mounted on said container in its folded position. The packaging may be a blister. Alternatively, the packaging may be an envelope surrounding the container and the piston rod folded on said container: the envelope may have a substantially cylindrical shape and may be a rigid tube.

Another aspect of the present invention is a method for manufacturing a compact prefilled injection device from a kit as described above comprising the following steps:
- filling said tubular barrel with a product to be injected and closing said tubular barrel at its distal end with a cap and its proximal end with a piston,
- mounting said piston rod on said container by lodging said junction element within said tubular barrel proximally from said piston, with the distal end of said barrel facing the proximal end of said piston,
- optionally attaching the distal end of said junction element to said piston,
- folding said first, second and optionally additional legs at the location of their bendable part over the proximal end of the tubular barrel with the proximal area of said legs extending parallel to the outer wall of said tubular barrel to obtain a compact prefilled injection device having a global cylindrical shape,
- optionally engaging the concave semi-circular shape of the transversal walls on the circular outer wall of the tubular barrel,
- optionally packaging said compact prefilled injection device in a substantially cylindrical envelope.

Figure 2:
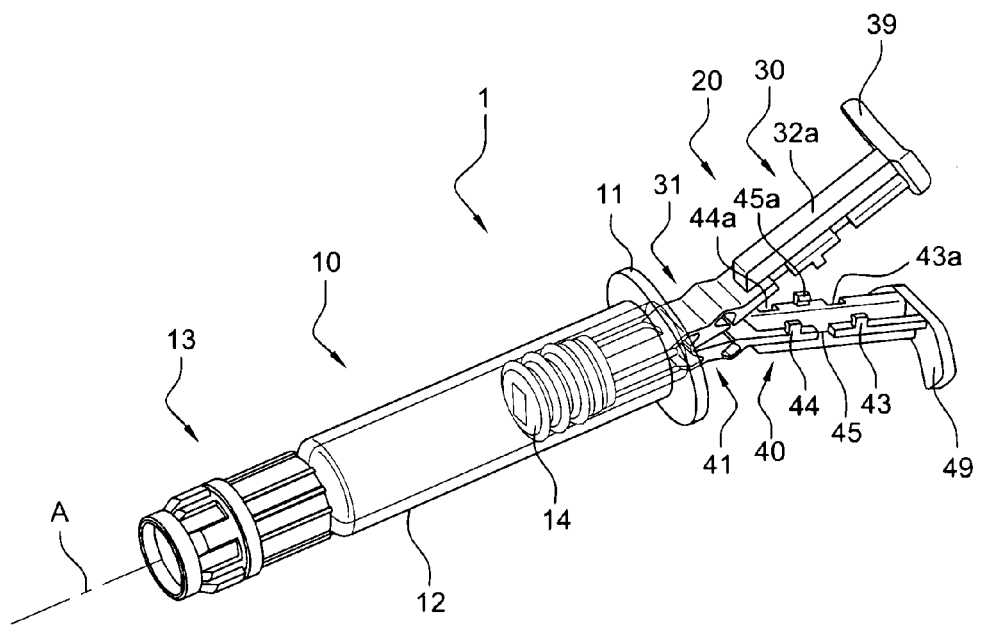
Figure 3:
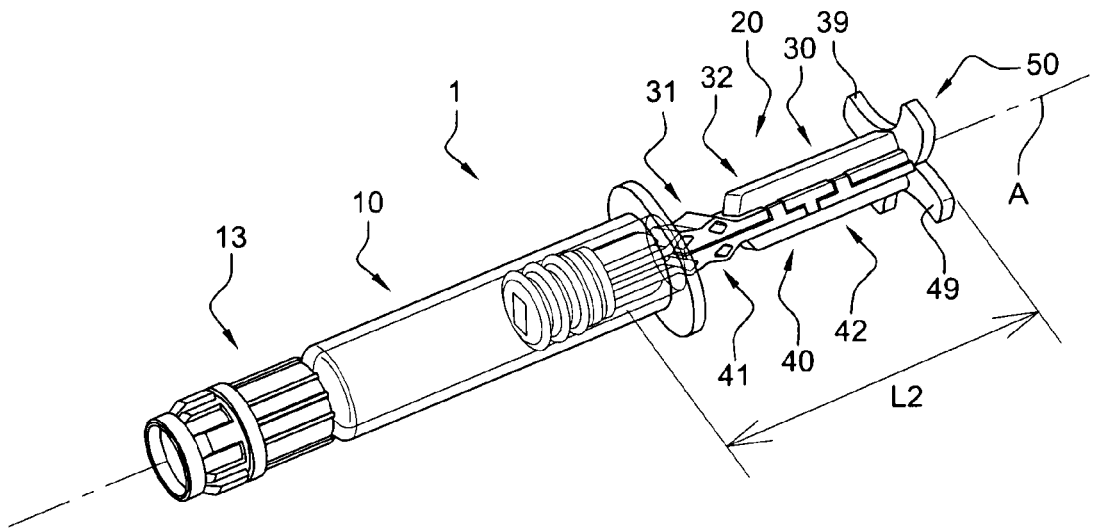
Figure 4:
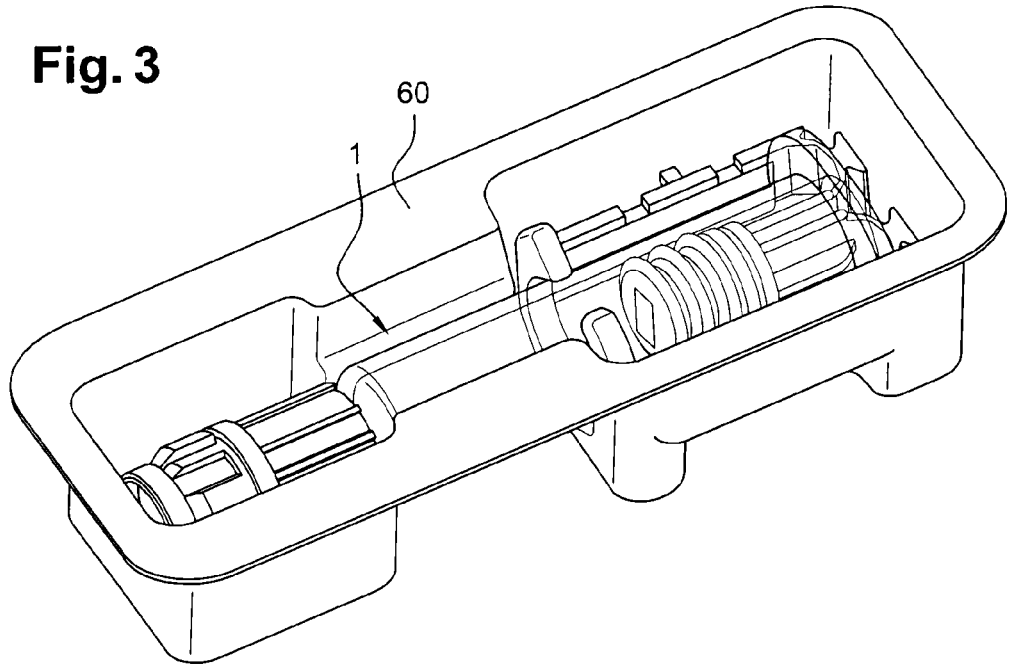
Figure 5:
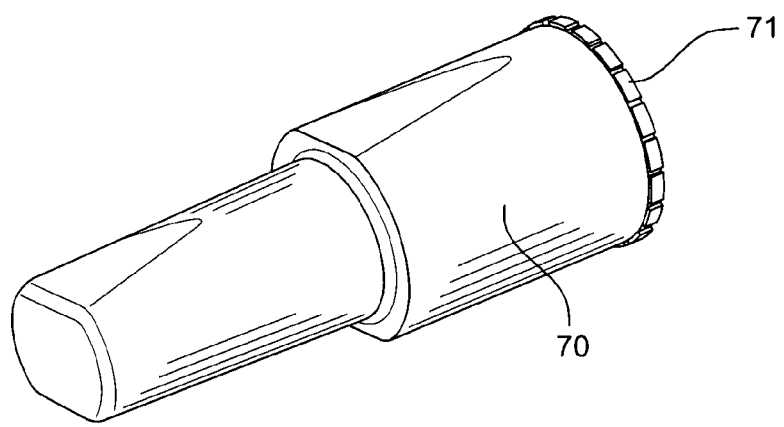
Figure 6:
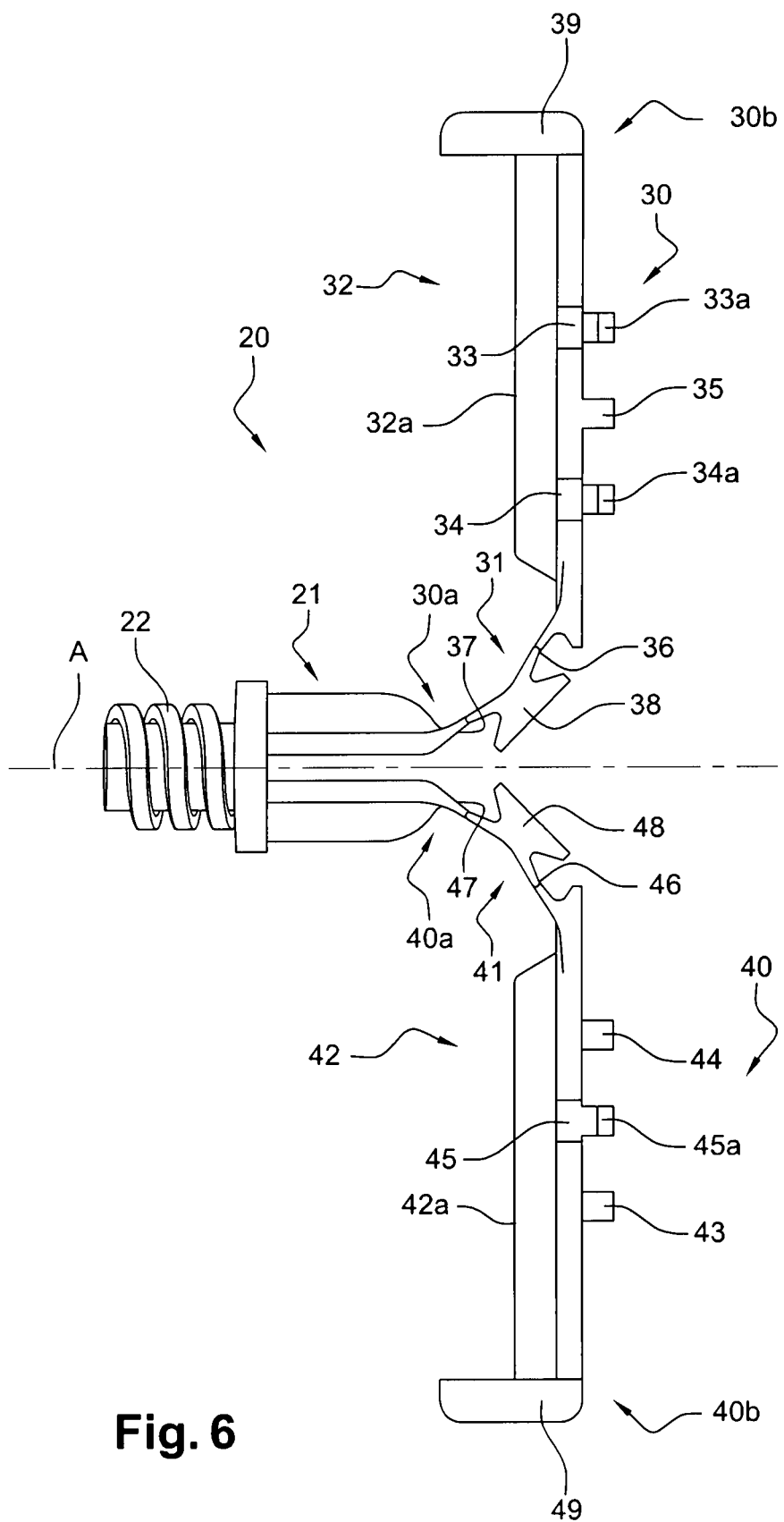
Figure 7:
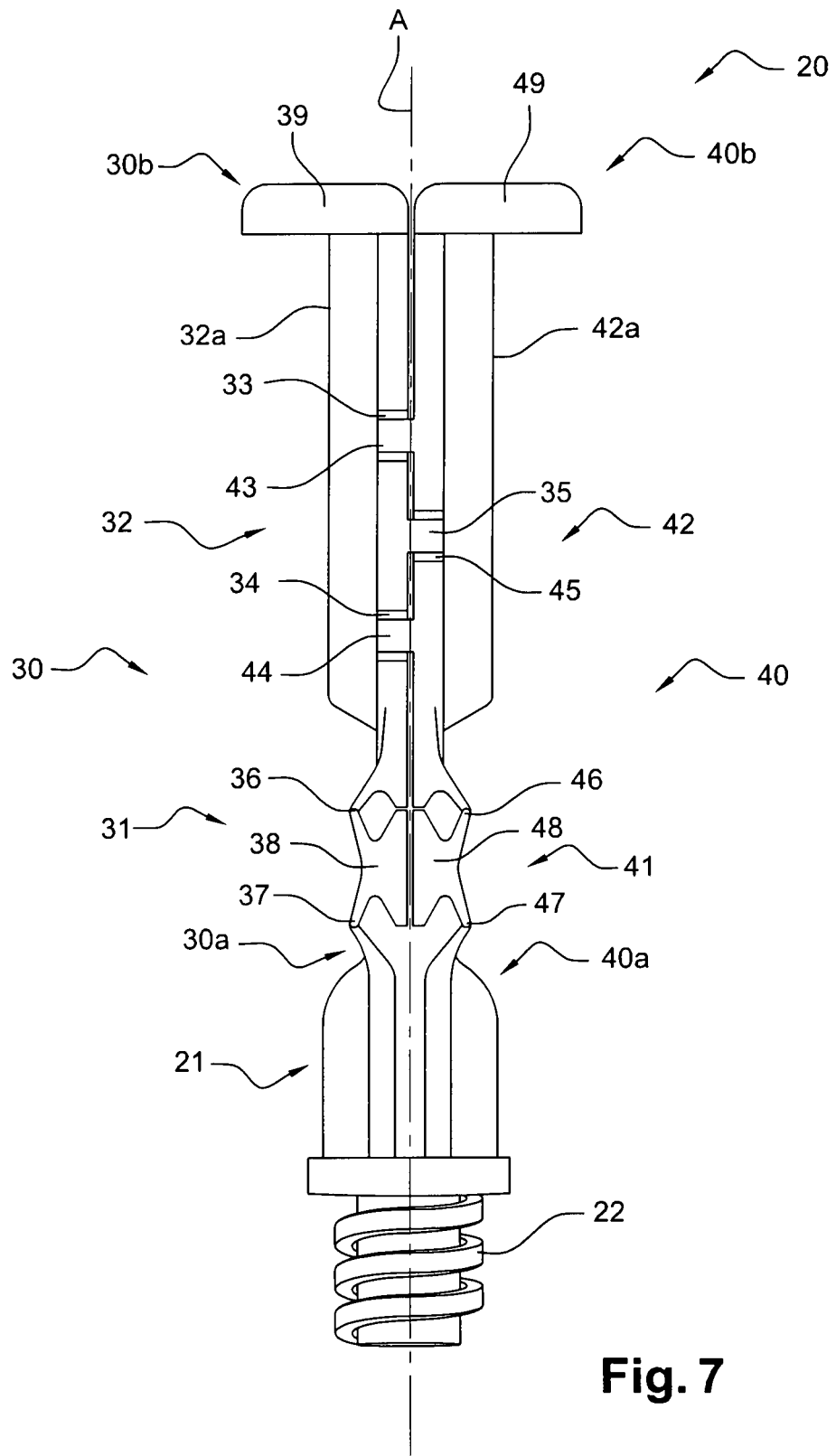
Figure 8:
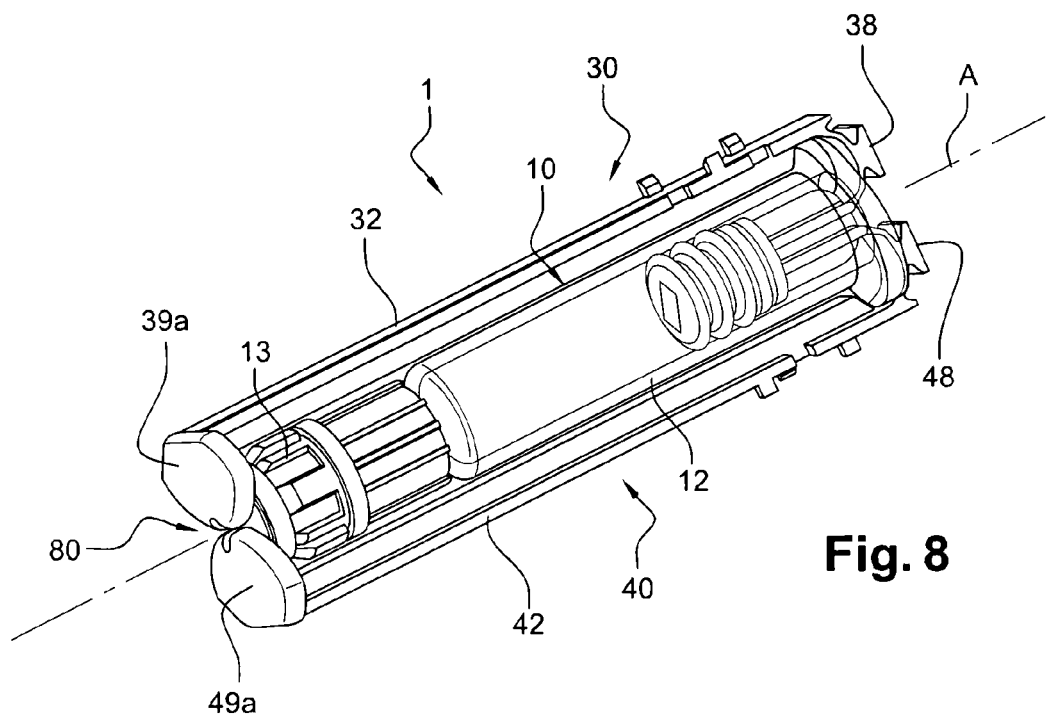
Figure 9:
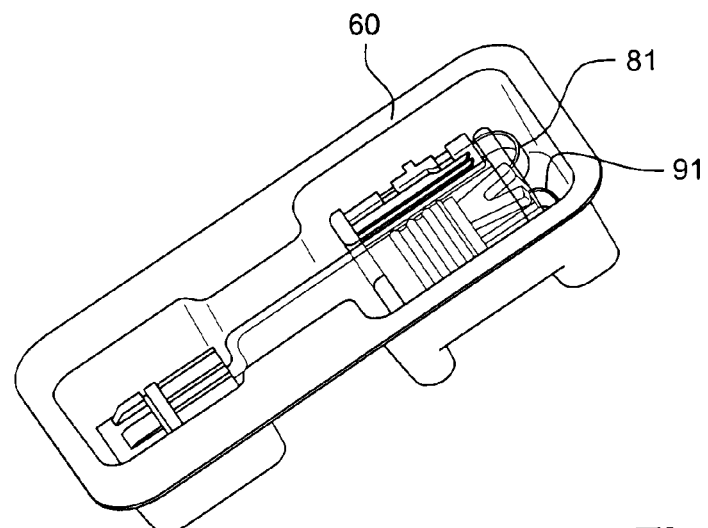
Figure 10:
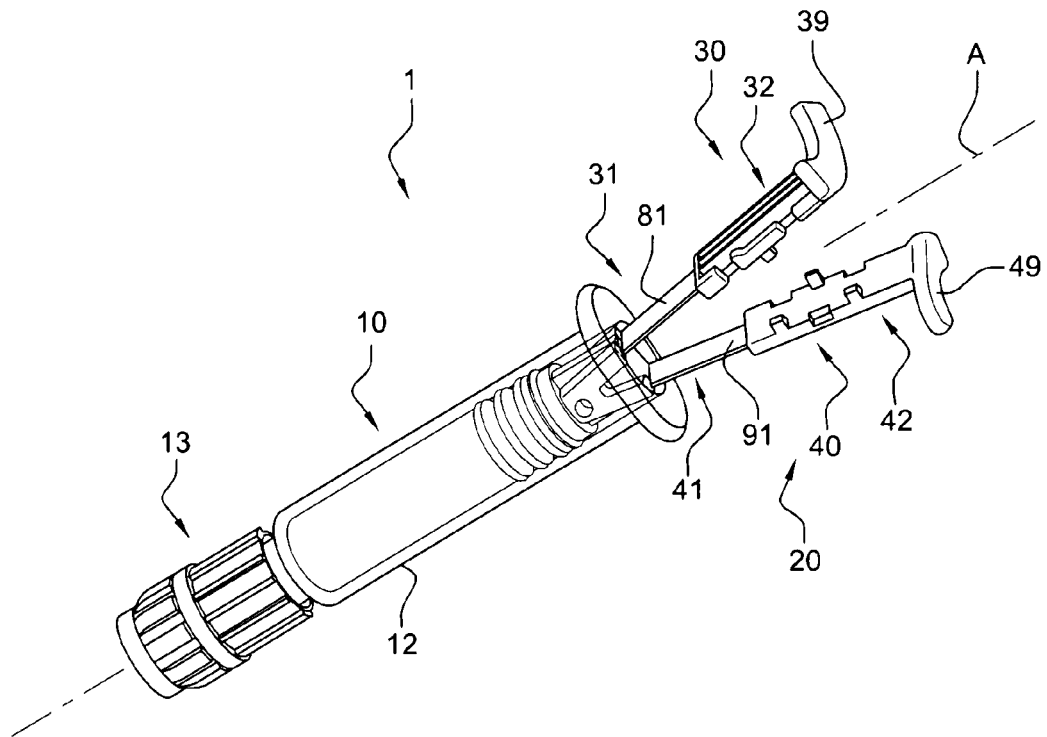
Figure 11:
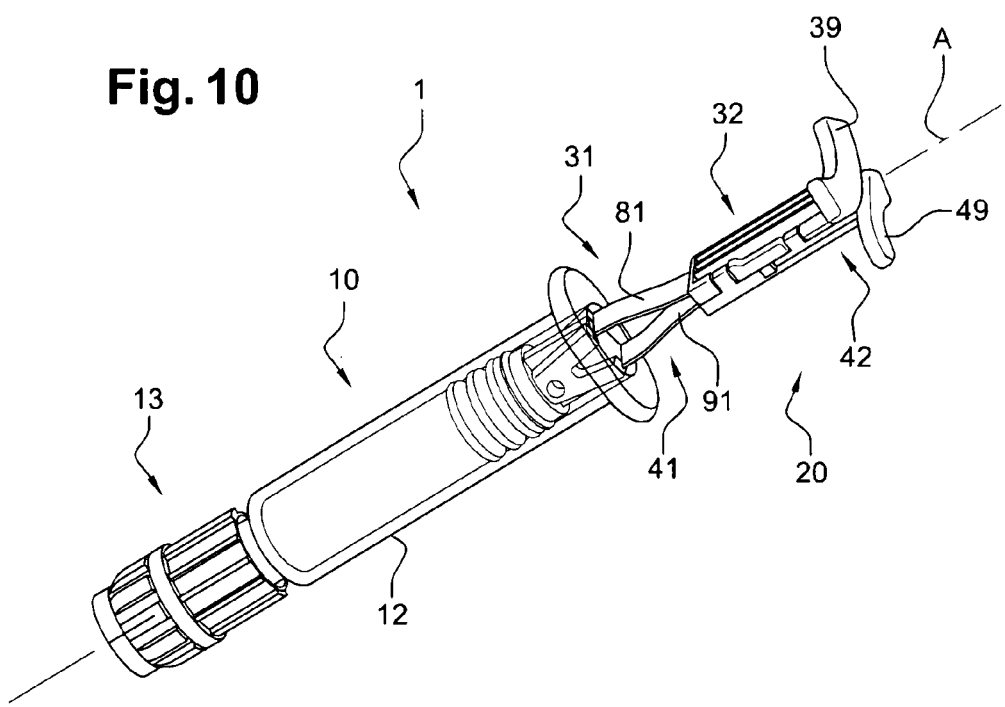

The present invention will now be described in greater detail with the aid of the following description and the appended drawings in which:

FIG. 1 represents a view in perspective of a piston rod of the invention in its folded position and mounted on a container of the kit of the invention, FIG. 2 represents a view in perspective of the kit of FIG. 1 in an intermediate position of the piston rod, FIG. 3 represents a view in perspective of the kit of FIG. 1 in the unfolded and ready-to-use position of the piston rod, FIG. 4 represents a view in perspective of the kit of FIG. 1 packaged in a blister, FIG. 5 represents a view in perspective of the kit of FIG. 1 packaged in an envelope, FIG. 6 is a side view of the piston rod of FIG. 1 in an intermediate position, FIG. 7 is a side view of the piston rod of FIG. 1 in its unfolded position with its two legs coupled to each other, FIG. 8 is view in perspective of an alternative of the kit of the invention, FIG. 9 is a view in perspective of another alternative of the kit of the invention, packaged in a blister, FIG. 10 is a view in perspective of the kit of FIG. 9, in an intermediate position of the piston rod, FIG. 11 is a view in perspective of the kit of FIG. 9, in the unfolded position of the piston rod with its two legs coupled to each other.

With reference to FIGS. 1-3, is shown a kit 1 of the invention comprising a container 10 in combination with a piston rod 20 according to the invention. On these figures, the piston rod 20 is mounted on the container 10 in order to form an injection device.

On the example shown, the container 10 is a syringe body formed of a tubular barrel 12 provided at its proximal end with a flange 11 (see FIG. 2). The flange 11 is intended to constitute a bearing surface for the fingers of the user at the time of performing the injection. The distal end of the container 10 is provided with a port for receiving an injection needle: in the example shown on the Figures, this port and this needle are not visible since the distal end of the container 10 is closed with a cap 13. Thanks to the cap 13 and to the piston 14 lodged within the tubular barrel 12 in the proximal area of the barrel, the container 10 can be prefilled with product to be injected, such as a medicine for example. The tubular barrel 12 may be made out of glass or plastic, preferably transparent.

With reference to FIGS. 1-3, the piston rod 20 is mounted on the container 10: in the example shown, the piston rod 20 is attached at its distal end to the piston 14. In other embodiments, the distal end of the piston rod 20 may simply face or contact the piston 14, without being attached to it.

As appears from these Figures, the piston rod 20 has a longitudinal axis A and is capable of being switched from a folded position, shown on FIG. 1, in which the piston rod 20 has a first length L1 measured along said longitudinal axis A and a globally compact cylindrical shape aligned on the longitudinal axis A, to an unfolded position, as shown on FIG. 3, in which the piston rod 20 has a second length L2 measured along the longitudinal axis A and an elongated shaft shape also aligned on the longitudinal axis A, and in which the piston rod 20 is ready for use. L1 is less than L2. On FIG. 2 is shown the piston rod 20 in an intermediate position that will be described later in relation with the operation of reconstitution of an injection device from the kit of the invention.

With reference to FIGS. 6 and 7 the piston rod 20 of FIGS. 1-3 is shown on its own respectively in an intermediate position and in its unfolded position for purposes of clarity. With reference to these Figures, the piston rod 20 comprises a first leg 30 and a second leg 40 having the same length and facing each other, and joined together at their respective distal ends (30a, 40a) at a fixed junction element 21 forming the distal part of the piston rod 20. As will appear from the description below, the first and second legs (30, 40) are capable of being connected to each other or on the contrary freed from one another at areas of their respective proximal regions, in order to either constitute a rigid shaft for the piston rod 20 in its unfolded position for use for injection, or constitute two free members capable of being folded on themselves, for example along the outer wall of the tubular barrel 12 when the piston rod 20 is mounted on the container 10.

Each leg (30, 40) comprises a bendable part (31, 41) separating the distal end (30a, 40a) of said leg from an area (32, 42) of said leg, proximally spaced apart from said bendable part (31, 41). Said area is called hereinafter the proximal area (32, 42) of said leg (30, 40). As appears from FIGS. 6 and 7, the proximal area 32 of the first leg 30 comprises a first recess 33 and a second recess 34, axially spaced apart from each other. The expression "axially spaced" is used here with reference to the longitudinal axis A in the unfolded position of said piston rod 20, as shown on FIG. 7. Located between the first and the second recesses (33, 34) is a peg 35. The proximal area 42 of the second leg 40 is provided with a first peg 43 and a second peg 44 axially spaced apart from each other and respectively facing the recesses (33, 34) of the proximal area 32 of the first leg 30 when the piston rod 20 is in its unfolded position as shown on FIG. 7. Located between the first and second pegs (43, 44) of the proximal area 42 of the second leg 40 is located a recess 45: as shown on FIG. 7, the recess 45 of the second leg 40 faces the peg 35 of the first leg 30 when the piston rod 20 is in its unfolded position.

Actually, as shown on FIG. 7, when the piston rod 20 is in its unfolded position ready for use, the peg 35 of the first leg 30 is engaged in the recess 45 of the second leg 40 and the pegs (43, 44) of the second leg 40 are engaged in the recesses (33, 34) of the first leg 30, the pegs (43, 44, 35) and recesses (33, 34, 45) forming snap fit means for connecting the proximal area 32 of the first leg 30 to the proximal area 42 of the second leg 40. The pegs and recesses here described constitute coupling means comprising three axially spaced fixing means each made of snap-fit means, the first fixing means being the snap-fit means made of the couple formed by the first recess 33 of the first leg 30 and the first peg 43 of the second leg 40, the second fixing means being the snap-fit means made of the couple formed by the peg 35 of the first leg 30 and the recess 45 of the second leg 40, and the third fixing means being the snap-fit means made of the couple formed by the second recess 34 of the first leg 30 and the second peg 44 of the second leg 40.

The first fixing means (33, 43), the second fixing means (35, 45) and the third fixing means (34, 44) are therefore axially spaced apart from one another in the unfolded position of the piston rod 20. Such an arrangement allows a reliable connection of the proximal area 32 of the first leg 30 to the proximal area (42) of the second leg 40, when the piston rod 20 is in its unfolded position as shown on FIG. 7. In embodiments not shown, the coupling means may comprise two fixing means axially spaced apart from one another. In the embodiment of FIGS. 1-3 and 6-7, the coupling means actually comprise six fixing means, three fixing means (33,43; 35,45; 34,44) as described above on one lateral side of the piston rod 20, and three other fixing means (33a,43a; 45a; 34a,44a) facing the first three fixing means but located on the other lateral side of the piston rod 20.

In embodiments not shown, the coupling means may be adhesive means, such as a plurality of points of glue located on the proximal area of one leg and axially spaced from each other.

With reference to FIG. 7, when the piston rod 20 is in its unfolded position with the pegs (43, 44, 35) engaged in the recesses (33, 34, 45), the proximal area 32 of the first leg 30 is blocked in translation with respect to the proximal area 42 of the second leg 40 and vice-versa. As a consequence, in this position, the proximal area 32 of the first leg 30 and the proximal area 42 of the second leg 40 are coupled to each other in a safe way, thereby forming a rigid shaft for the piston rod 20. The piston rod 20 may then be used for pushing distally the piston 14 without any risk that the proximal area 32 of the first leg 30 slide with respect to the proximal area 42 of the second leg 40, thereby jeopardising the efficiency of the injection.

With reference to FIGS. 6 and 7, the first leg 30 comprises a bendable part 31 formed by a first transversal hinge 36 and a second transversal hinge 37 axially spaced apart from each other. The bendable part 41 of the second leg 40 is also provided with a first transversal hinge 46 and a second transversal hinge 47 axially spaced from each other. The fact that for each leg (30, 40), the two transversal hinges (36, 37; 46, 47) are axially spaced apart from each other allows the leg to be folded on itself, in the folded position of the piston rod 20 as shown on FIG. 1, so that the proximal area (32, 42) of each leg (30, 40) faces the junction element 21 in such a position. Indeed, when the piston rod 20 is mounted on a container 10 having a flange 11 as shown on FIGS. 1 and 2, the space present between the first transversal hinge (36, 46) and the second transversal hinge (37, 47) on each leg (30, 40) enables the bendable part (31, 41) to design around the flange 11 so that the proximal area (32, 42) of each leg (30, 40) can then be located parallel to the wall of the container 10, thereby limiting as much as possible the volume occupied by each leg (30, 40).

Moreover, with reference to FIGS. 6 and 7, on the first leg 30, the two transversal hinges (36, 37) are linked to each other by a rigid bridge 38. The two transversal hinges (46, 47) of the second leg 40 are also linked to each other by a rigid bridge 48.

As appears from FIG. 7, when the piston rod 20 is in its unfolded position, the rigid bridge 38 of the first leg 30 and the rigid bridge 48 of the second leg 40 face each other, thereby reinforcing this region of the reconstituted piston rod 20 and contributing to obtaining a rigid shaft for the piston rod 20.

With reference to FIGS. 6 and 7, the first leg 30 and the second leg 40 are each provided at their proximal end (30b, 40b) with a transversal wall (39, 49). As appears from FIGS. 1-3, the transversal walls (39, 49) have each substantially the form of a moon crescent, with the convex part of the moon crescent being directed towards the longitudinal axis A in the unfolded position of the piston rod 20: as a consequence, in the folded position of the piston rod 20, as shown on FIG. 1, the concave semi-circular shape of each transversal wall (39, 49) is directed towards the longitudinal axis A and matches the circular outer shape of the barrel 12 forming the container 10, thereby limiting the volume occupied by each leg (30, 40) around the container 10. The shape of each transversal wall (39, 49) is therefore complementary in shape to the outer shape of the barrel 12 and each transversal wall (39, 49) is in a nesting relationship with the barrel 12.

In an embodiment not shown, in the folded position of the piston rod 20 mounted on the container 10 as shown on FIG. 1, the transversal wall 39 of the first leg 30 could be linked to the transversal wall 49 of the second leg 40 by at least one breakable link, preferably by two breakable links, each breakable link connecting for example an extremity of one moon crescent shaped transversal wall (39, 49) to an extremity of the other moon crescent shaped transversal wall (49, 39), thereby forming a tamper evidence system in a storage position of the kit of the invention. Indeed the breakable links, forming globally with the two transversal walls (39, 49) a ring surrounding the external surface of the container 10, would need to be broken before using the injection device.

On each leg (30, 40), the proximal area (32, 42) is further provided with a reinforcing element under the form of an outer ridge (32a, 42a).

On the example shown, the junction element 21 of the piston rod 20 is provided at its distal end with attaching means, a screw 22 on the example shown, for attaching the piston rod 20 to the piston 14.

The piston rod 20, and in particular the legs (30, 40) may be made of any material allowing on one hand the necessary flexibility of the bendable parts (31, 41) to enable the folding of the legs of the piston rod 20 and on the other hand the minimum rigidity required for pushing the piston once the piston rod 20 is reconstituted. Examples of material suitable for the manufacture of the piston rod of the invention are polyolefins such as polyethylene or polypropylene. In embodiments, the transversal hinges (36, 37, 46, 47) are made of a material different than that of the rest of the legs: in embodiments the transversal hinges (36, 37, 46, 47) may be made of thermoplastic polyethylene while the rest of the legs (30, 40) may be made of polystyrene or polycarbonate.

The reconstitution of an operable injection device obtainable with a piston rod 20 and/or a kit 1 of the invention will now be described with reference to FIGS. 1-3.

The piston rod 20 may be provided to the user already mounted on the prefilled container 10, as shown on FIG. 1, the piston rod 20 being in its folded position, with the proximal areas (32, 42) of the two legs (30, 40) folded along the outer wall of the tubular barrel 12, the concave parts of the transversal walls (39, 49) being in contact with the outer wall of the tubular barrel 12 and being in a nesting relationship with said tubular barrel 12. In order to reconstitute the piston rod 20 ready for use, the user first breaks the one or more breakable links as described above when present, then unfolds the two legs (30, 40) as shown on FIG. 2. He then connects the first leg 30 to the second leg 40 by snap-fitting together the proximal area 32 of the first leg 30 to the proximal area 42 of the second leg 40 by engaging the pegs into the recesses as explained above, thereby reconstituting the piston rod 20 in its unfolded position as shown on FIG. 3. As indicated above, the shaft thereby obtained is rigid and reliable and may be used for pushing distally the piston 14 within the tubular barrel 12 safely. Moreover, as it appears clearly from FIG. 3, the two transversal walls (39, 49) now constitute an adequate and reliable pushing surface 50 for the user.

In order to perform the injection, the user removes the cap 13 and pushes distally on the pushing surface 50 formed by the transversal walls (39, 49). As explained above, the presence of at least two fixing means axially spaced apart from each other in the proximal areas (32, 42) of the legs (30, 40) and of the rigid bridges (38, 48) linking together the respective two transversal hinges (36, 37; 46, 47) of the bendable parts (31, 41) of the legs (30, 40) allows obtaining a sure and reliable elongated shaft not deviating from the longitudinal axis A when the user pushes distally on the piston rod 20.

With reference to FIG. 4 is shown the kit 1 of FIG. 1, in the folded position of the piston rod 20, in a packaging which is a blister 60. As it appears clearly on this Figure, the packaged kit 1 has a compact shape and occupies as little volume as possible. In addition, due to its relatively regular and compact volume, the packaged kit 1 is easy to pile up with other similar packaged kits: it is then possible to store a large number of pre-packaged kits in inventories of hospitals or pharmacies.

With reference to FIG. 5 is shown an alternative embodiment of a packaging: in this Figure, the kit 1, which is not visible, is packaged in a rigid envelope 70 having globally the outer cylindrical shape corresponding to the shape of the kit in the folded position of the piston rod 20, that is substantially two tubes of two different diameters, closed by a cap 71. As it appears clearly from this Figure, the packaged kit shows a very compact shape and volume and can be stored easily with a large number of other similar packaged kits.

With reference to FIG. 8 is shown an alternative embodiment of the kit 1 of FIGS. 1-6, where the proximal regions of the legs extend beyond the distal end of the container in the folded position of the piston rod. The references designating the same elements as in FIGS. 1-6 have been maintained. As shown on this Figure, the proximal area 32 of the first leg 30 and the proximal area 42 of the second leg 40 have the same length and their distal ends extend beyond the distal end of the container 10, i.e. beyond the distal end of the cap 13 closing the distal end of container 10 in the folded position of the piston rod 20. In this embodiment the moon crescent shaped transversal walls (39, 49) of FIGS. 1-6 are replaced by transversal walls (39a, 49a) having each an oval shape: this oval shape allows the two transversal walls (39a, 49a) to join each other at a common point where they are linked to each other by a breakable link 80. As a consequence, as appears from FIG. 8, the container 10 is totally surrounded by the piston rod 20 and a user must break the breakable link 80 so as to detach the first leg 30 from the second leg 40 in order to reconstitute the piston rod 20 for performing the injection. The two transversal walls (39a, 49a) linked together constitute a breakable protection wall covering the distal end of the cap 13. The breakable link 80 constitutes a tamper proof means informing a user whether the injection device has already been opened or not.

A blister or a rigid envelope having globally the shape of a tube closed at both ends, for example by one or more caps, can be used to package the kit 1 shown on FIG. 8 in order to optimize the volume of the storage of such kits.

On FIGS. 9-11 is shown another embodiment of the piston rod of the invention, where the bendable parts of the legs are under the form of metallic blades. The references designating the same elements as in FIGS. 1-6 have been maintained. In this embodiment, the bendable part (31, 41) of each leg (30, 40) is formed of an elastic metallic blade (81, 91). The metal constituting the elastic metallic blade (81, 91) may be chosen from any metal showing an elasticity allowing the blade to be flexed and folded on itself so as to adopt a U shape, as shown on FIG. 9, under stress, and then allowing the blade to come back automatically to its rest shape when no more stress is applied. For example, the metal is selected from steels and superelastic materials such as shape memory alloys.

In such an embodiment, the user is provided with the kit 1 packaged in a blister 60 as shown on FIG. 9, with the piston rod 20 maintained in its folded position by means of the lateral walls of the blister 60 exerting a pressure on the proximal areas (32, 42) of the legs (30, 40), thereby stressing the elastic metallic blades (81, 91) in their U shape. In this embodiment, the proximal areas (32, 42) of the legs (30, 40) are provided with the same coupling means comprising pegs and recesses as described for the embodiment of FIG. 1. For sake of clarity, the references of these pegs and recesses are not reported on FIGS. 9-11. When the user removes the kit 1 from the blister 60, no more pressure is exerted on the proximal areas (32, 42) of the legs (30, 40) and the elastic metallic blades (81, 91) come back to their rest shape, which is an intermediate position of the piston rod 20, as shown on FIG. 10. The user then connects together the proximal area (32) of the first leg (30) and the proximal area (42) of the second leg (40) by snap-fitting the pegs in the recesses as explained for embodiment of FIGS. 1-6. Such an embodiment minimizes the number of actions the user is required to perform in order to reconstitute the piston rod 20 ready for use.

As appears from FIG. 9, the packaged kit of embodiment of FIGS. 9-11 occupies a restricted volume and has an outer compact shape allowing it to be stored easily and simply with a large number of other packaged kits.

In such an embodiment, like for the embodiment of FIG. 1, in the folded position of the piston rod 20 mounted on the container 10 as shown on FIG. 9, the transversal wall 39 of the first leg 30 could be linked to the transversal wall 49 of the second leg 40 by at least one breakable link, preferably by two breakable links, each breakable link connecting for example an extremity of one moon crescent shaped transversal wall (39, 49) to an extremity of the other moon crescent shaped transversal wall (49, 39), thereby forming a tamper evidence system in a storage position of the kit of the invention.

The present invention also relates to a method for manufacturing a compact prefilled injection device from a kit 1 as described above comprising the following steps:
- filling a tubular barrel 12 of a container 10 with a product to be injected and closing said tubular barrel at its distal end with a cap 13 and its proximal end with a piston 14,
- mounting a piston rod 20 according to the present invention on said container 10 by lodging a junction element 21 within said tubular barrel 12 proximally from said piston 14, with the distal end of said barrel facing the proximal end of said piston 14,
- optionally attaching the distal end of said junction element 21 to said piston 14,
- folding said first, second and optionally additional legs (30, 40) at the location of their bendable part over the proximal end of the tubular barrel with the proximal area (32, 42) of said legs extending parallel to the outer wall of said tubular barrel 12 to obtain a compact prefilled injection device having a global cylindrical shape,
- optionally engaging the concave semi-circular shape of the transversal walls on the circular outer wall of the tubular barrel,
- optionally packaging said compact prefilled injection device in a blister 60 or a substantially cylindrical envelope 70.

As appears from the description above, the piston rod 20 and the kit 1 of the invention allow manufacturing an injection device that can be stored in a very compact configuration. Such compact packaged injection devices may be stored easily and may be stacked up with other similar compact packaged injection devices in very limited space. Such compact packaged injection devices are of particular interest for pharmacies and hospitals where a large number of such injection devices must be stored.

The invention claimed is:

1. A piston rod for an injection device, said piston rod comprising a first and a second legs, each leg comprising a bendable part and extending substantially proximally from a junction element at which a distal end of each of the first and second legs meet, each leg being capable of being folded at the location of its bendable part, said piston rod having a globally elongated shape substantially aligned on a longitudinal axis (A) and being in one of a folded position, in which said piston rod has a first length, and an unfolded position, in which said piston rod has a second length that is different from said first length,
wherein when said piston rod is in said folded position, the first and second legs are folded at their respective bendable part, and an exterior surface portion of each leg, proximally spaced from said bendable part, faces the junction element,
wherein when said piston rod is in said unfolded position, said exterior surface portions of said first and second legs face each other,
said piston rod further comprising a coupling mechanism for coupling said exterior surface portions directly with each other when said piston rod is in said unfolded position.

2. The piston rod according to claim 1, wherein the coupling mechanism includes at least a first coupling portion and a second coupling portion, said first and second coupling portions being axially spaced apart from each other in said unfolded position of the piston rod.

3. The piston rod according to claim 2, wherein the coupling mechanism further includes a third coupling portion, said first, second and third coupling portions being axially spaced apart from one another in said unfolded position of the piston rod.

4. The piston rod according to claim 1, wherein the coupling mechanism is located on said exterior surface portion of only one of said first and second legs.

5. The piston rod according to claim 1, wherein the coupling mechanism is located partly on said exterior surface portion of said first leg and partly on said area of said second leg.

6. The piston rod according to claim 1, wherein said coupling mechanism comprises a peg and a recess engageable with each other when said piston rod is in said unfolded position, said peg being located on said exterior surface portion of one of said first and second legs, said recess being located on said external surface portion of the other one of said first and second legs.

7. The piston rod according to claim 1, wherein at least one of said first and second legs is provided at its proximal end with a transversal wall.

8. The piston rod according to claim 7, wherein each of said first and second legs is provided at its proximal end with a transversal wall.

9. The piston rod according to claim 8, wherein each of said transversal wall has a semi-circular concave shape, said semi-circular concave shape being directed towards the longitudinal axis (A) in the folded position of the piston rod.

10. The piston rod according to claim 1, wherein each of said bendable parts comprises two hinges axially spaced apart from each other in the unfolded position of the piston rod.

11. The piston rod according to claim 10, wherein said two hinges are linked to each other by a bridge.

12. The piston rod according to claim 11, wherein said bridge of the first leg faces said bridge of the second leg when said piston rod is in its unfolded position.

13. The piston rod according to claim 1, wherein each of said bendable parts is made of an elastic metallic blade.

14. The piston rod according to claim 1, wherein said junction element comprises at its distal end piston attaching mechanism.

15. A kit comprising a piston rod according to claim 1, further comprising a container intended to receive a product to be injected, said container comprising a tubular barrel provided at its distal end with a port intended to receive an injection needle, said product being intended to be expelled from said tubular barrel under distal displacement of a piston movable within said tubular barrel by said piston rod.

16. The kit according to claim 15, wherein the tubular barrel is prefilled with the product to be injected, said tubular barrel being closed at its distal end with a cap and at its proximal end by said piston.

17. The kit according to claim 16, wherein said piston rod is mounted on said container, the junction element of the piston rod being lodged within said tubular barrel proximally from said piston with the distal end of said junction element facing the proximal end of said piston, said piston rod being in its folded position.

18. A kit according to claim 15, wherein the shape of a transversal wall is complementary in shape to an outer shape of said tubular barrel, the complementary shape of the transversal wall and the outer shape of said tubular barrel enabling a nesting relationship between the transversal wall and said tubular barrel when said piston rod is in its folded position.

19. A kit according to claim 18, wherein said two transversal walls are linked to each other by at least a breakable link when said piston rod is in its folded position.

20. A kit according to claim 19, wherein the proximal end of each of said first and second legs extends beyond the distal end of said barrel.

21. A kit comprising a piston rod according to claim 1, further comprising packaging for receiving said piston rod mounted on said container in its folded position.

22. A piston rod for an injection device, the piston rod comprising:
   a first leg having a first leg distal end and a first leg proximal end, and a first leg rod portion extending between the first leg distal end and the first leg proximal end, the first leg rod portion having a first leg bendable portion; and
   a second leg having a second leg distal end and a second leg proximal end, and a second leg rod portion extending between the second leg distal end and the second leg proximal end, the second leg rod portion having a second leg bendable portion,
   the piston rod bendable about the first leg bendable portion and the second leg bendable portion between a folded position in which the piston rod has a first effective length and an unfolded position in which the piston rod has a second effective length, the first effective length less than the second effective length,
   wherein, with the piston rod in the folded position, the first leg proximal end faces the first leg distal end and the second leg proximal end faces the second leg distal end such that the first leg and the second leg are positioned parallel relative to one another, and
   wherein, with the piston rod in the unfolded position, the first leg proximal end is aligned with the first leg distal end along a longitudinal axis, the second leg proximal end is aligned with the second leg distal end along the longitudinal axis, and the first leg and the second leg are directly coupled with each other.

23. The piston rod of claim 22, wherein the first leg distal end and the second leg distal end meet at a junction element.

24. The piston rod of claim 22, further comprising:
   a first leg first connection portion on a portion of the first leg; and
   a second leg first connection portion on a portion of the second leg,
   wherein, with the piston rod in the unfolded position, the first leg first connection portion is engaged with the second leg first connection portion.

25. The piston rod of claim 24, further comprising:
   a first leg second connection portion on a second portion of the first leg, the first leg second connection portion spaced from the first leg first connection portion; and
   a second leg second connection portion on a second portion of the second leg, the second leg second connection portion spaced from the second leg first connection portion,
   wherein, with the piston rod in the unfolded position, the first leg second connection portion is engaged with the second leg second connection portion.

26. The piston rod of claim 25, further comprising:
   a first leg third connection portion on a third portion of the first leg, the first leg third connection portion spaced from the first leg first connection portion and the first leg second connection portion; and
   a second leg third connection portion on a third portion of the second leg, the second leg third connection portion spaced from the second leg first connection portion and the second leg second connection portion,
   wherein, with the piston rod in the unfolded position, the first leg third connection portion is engaged with the second leg third connection portion.

* * * * *